United States Patent [19]

Brown et al.

[11] 4,329,298
[45] May 11, 1982

[54] ISOMERIZATION OF JOJOBA OIL AND PRODUCTS THEREOF

[75] Inventors: James H. Brown, Chappaqua; Harry Olenberg, Bronx, both of N.Y.

[73] Assignee: Jojoba Growers & Processors Inc., New York, N.Y.

[21] Appl. No.: 177,971

[22] Filed: Aug. 15, 1980

[51] Int. Cl.$^3$ .............................................. C11C 3/14
[52] U.S. Cl. ............................ 260/405.6; 106/243; 106/270; 252/8.57
[58] Field of Search ................. 260/405.6; 106/243, 106/270, 244

[56] References Cited

U.S. PATENT DOCUMENTS 2,350,082  5/1944  Taussky .......................... 260/405.6
3,065,248  11/1962  Brown et al. .................... 260/405.6

FOREIGN PATENT DOCUMENTS 1211158  2/1966  Fed. Rep. of Germany ... 260/405.6

Primary Examiner—Lorenzo B. Hayes
Attorney, Agent, or Firm—Wolder, Gross & Yavner

[57] ABSTRACT

A process for isomerization of natural jojoba oil, a wax-type ester is described. It is based on contacting jojoba oil, essentially all cis-configuration with an acidic bentonite-type clay at temperatures in the range 150°–350° C. The resulting isomerates, predominately of trans-configuration have melting points in the range 25° to about 44° C.

18 Claims, 1 Drawing Figure

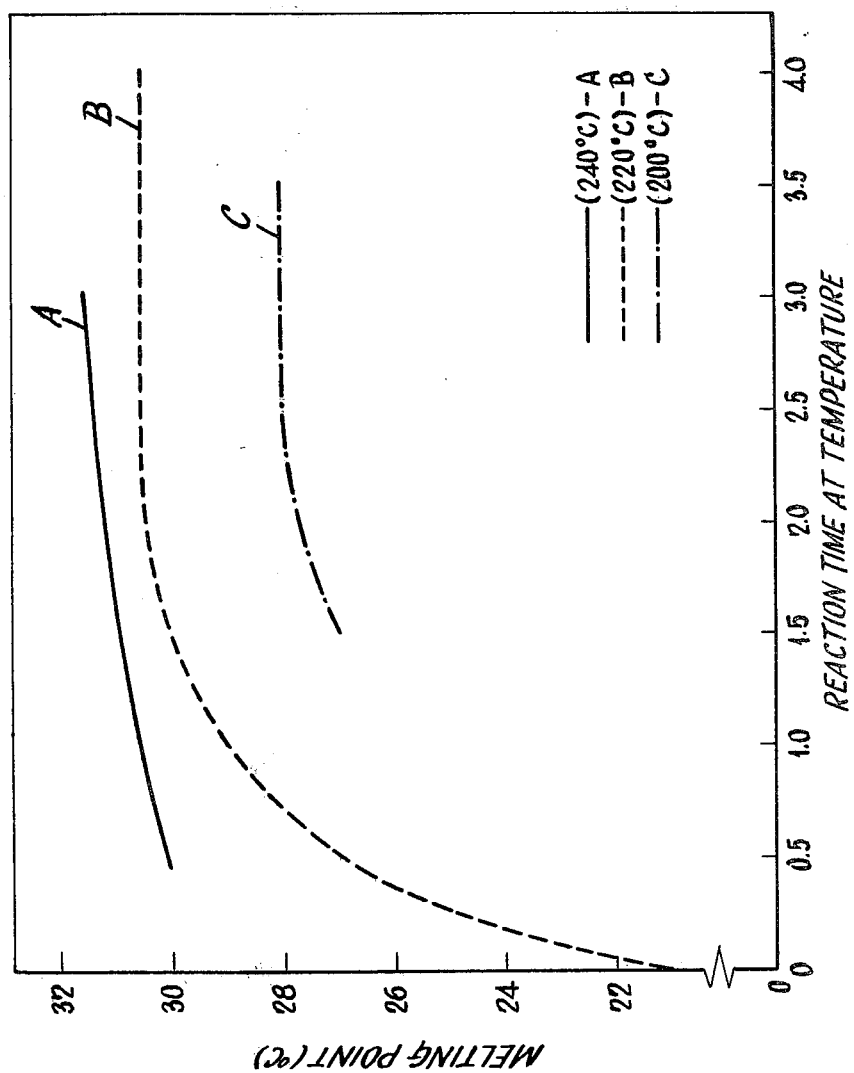

ISOMERIZATION OF JOJOBA OIL AND PRODUCTS THEREOF

FIELD OF THE INVENTION

This invention relates to jojoba oil modification and more particularly to the controlled isomerization of jojoba oil to isomerates having softening points in the range 25°–40° C. and suitable for topical application.

BACKGROUND OF THE INVENTION

As set forth in the NRC report of the National Academy of Science entitled "Products from Jojoba" (1975) and subsequent publications by Miwa et al, of the Northern Regional Research Center USDA and Wisniak of Ben Gurion University as reported in *Jojoba Happenings* published by The Office of Arid Land Studies, The University of Arizona, jojoba oil is a unique oil and a potential replacement for the sperm whale oil formerly obtained from a disappearing and endangered whale species.

Jojoba nut oil differs from most other animal and vegetable oils in that it is not a fat but a liquid wax. Fats, including the seed oils of most other plants, are triglycerides (a mole of glycerol esterified with three moles of long-chain fatty acids). Jojoba and sperm oil are wax esters (one mole of a long-chain alcohol esterfied with one mole of a long-chain fatty acid). Jojoba oil is unique among vegetable oils, as sperm oil is unique among animal oils. Such a vegetable oil has never before been available to industry in commercially usable quantities.

The following characteristics make jojoba oil valuable: its natural purity and molecular simplicity and its stability; it is a non-drying oil, having high resistance to oxidation; it can be stored for years without becoming rancid; its lubricity; its unsaturation (double bonds).

The clear, unsaturated oil can be obtained by pressing or solvent-extraction methods used commercially to isolate vegetable oils from cotton seeds, soybeans, copra and corn.

Such jojoba oil extracts usually have the same wax-ester composition. The acids and alcohols that make up these esters do not vary appreciably with location, soil type, rainfall, or altitude. Moreover, the oil does not change in composition during storage.

Jojoba oil is composed almost entirely of esters of high molecular weight $C_{18-24}$, straight-chain monoethylenic acids and monoethylenic alcohols, for example, erucyl 11-cis-eicosenoate of the formula:

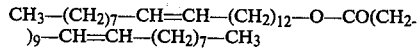

These unsaturated acids are a mixture of cis-11-eicosenoic ($C_{20}$) and cis-13-docosenoic ($C_{22}$) erucic, with small quantities of oleic ($C_{18}$) and nervonic ($C_{24}$) acids. The unsaturated alcohols are a mixture of cis-11-eicosenol, cis-13-docosenol and cis-15 tetracosenol, with small quantities of alcohols of lower molecular weight. Note that all the alcohols and acids are primarily of the cis configuration.

The conventional position for a double bond in other natural fats or oils composed of $C_{18}$ acids is $\Delta 9$ i.e. between carbon 9 and 10 of each of the fatty acids, but jojoba oil has mainly $\Delta 11$ and $\Delta 13$ unsaturation in the alcohols and acids, because of the large amount of $C_{20}$ and $C_{22}$ chains. All of the jojoba monoenes can be placed in the $\omega$-9 acids or $\omega 9$ alcohols homologous series.

Jojoba oil is chemically more pure than most natural substances; 97 percent or greater liquid wax esters by gas chromatography. Yellow pigments in the oil can be removed with bleaching earths. The oil also has narrow range of wax-ester structures—over 83 percent $C_{20}$ and $C_{22}$ acids and alcohols.

Cis-to-trans-isomerization of the double bonds has been induced with selenium and nitrous oxide catalysts, producing up to 80 percent trans and 20 percent cis double bonds. The product is a soft solid with a melting point of about 44° C. The amount of such isomers formed can be controlled during these isomerizations by reaction time to obtain any melting point between that of the pure oil (7° C.) and 44° C. A product with a melting point close to that of the human body is desirable. However, both selenium and nitrous oxide previously used as catalysts present potential dermatological problems.

It is an object of this invention to provide a method for the cis-trans isomerization of jojoba oil to provide isomerates of jojoba oil having softening points in the range 25°–40° C.

It is a further object to provide such isomerates by a process whereby the products directly are of sufficient purity for topical application.

Another object is to provide jojoba isomerates having a softening point at about or just below body temperature for use in formulations for topical application to the skin and at other temperatures for other uses.

A further object is to provide isomerates suitable for leather treatment whereby the isomerate of jojoba oil may be incorporated into the hide or skin substrate at elevated temperatures in the liquid form but will revert to semi-solid form in the substrate upon cooling to normal use temperatures (below 35° C.).

These and other objects will be readily apparent from the description of the process and the products derived therefrom which follows.

THE INVENTION

The present invention provides a method for the preparation of isomerates of jojoba oil melting above about 25° C. which comprises the steps of contacting jojoba oil with an acidic, bentonite-type clay at temperature in the range 150°–350° C. for a time sufficient to isomerize the oil from the naturally occurring cis-configuration to the trans-configuration in amounts sufficient to provide an isomerate having a melting point in the range 25° to about 44° C.

DETAILED DESCRIPTION

The present invention is based on the discovery that acidic bentonite-type clays when contacted with jojoba oil initiate isomerization of the cis-configurations thereof to the transconfiguration above certain temperatures. At room temperature to about 150° C. there is little or no isomerization upon contact, even over extended (24 hour) period of time. However, at temperatures above about 150° C. the isomerization reaction begins to take place and accelerates upon increased temperatures. The isomerization can take place up to about 350° C.

The amount of isomerization of the oil may be followed by determining the melting point of the isomerate. Commercial jojoba oil melts at about 5°–9° C. Refined jojoba oil, substantially pure cis-configuration, melts at 7° C. The pure transconfigured oil is reported to melt at about 54° C. As the percentage isomerization increases the melting point of the oil increases. At the conditions of isomerization of the invention, the melting point of such isomerized oil is in the range 25°–30° C.

The amount of isomerization with the clay is temperature dependent provided that sufficient clay is present to promote the reaction. Clay amounts as little as 0.005 wt% will cause isomerization at low rates. The amount of clay needed to initiate the reaction at a creditable rate is about 0.5 wt% based on the weight of the oil. Preferably about two wt% of the clay should be used to provide suitable isomerization rates at each temperature. Suitable isomerization rates are those wherein the melting point of the isomerizate at a given contact temperature stabilizes and becomes substantially constant after about half to one and one half hour of contact with the catalyst.

The degree of isomerization, as measured by the melting point of the isomerate varies with the contact temperature. At contact temperatures of about 200° C., unrefined oil, in contact with 2 wt% of the preferred clays for at least one and one half hours, provides materials melting in the range 27°–28° C. At 220° C., the melting points range from about 29°–30.5° C. and at 240° C. from about 30°–31.5° C. Utilizing a refined jojoba oil, the melting points obtained are about two to three degrees higher.

The FIGURE shows the curve demonstrating the relationship of the isomerate melting point as a function of the reaction contact time and the reaction temperature. The amount of clay used in the reaction mass was two wt% of the oil introduced. The melting points of the isomerate at various temperatures and times was determined by standard methods. It will be noted that the melting point stabilizes at each contact temperature and even prolonged contact with the clay at the temperature has little effect on the melting point after the initial rise to stabilization of the melting point and consequent degree of isomerization.

The acidic bentonite-type clays that promote the isomerization at the stated temperature range are of the class that is well known for its use at lower temperatures for bleaching mineral and edible oils. These clays are of the montmorillonite crystalline form and have been treated with acid, usually HCl to modify the configuration and expand the total surface of the clay. Such acidic bleaching clays are generally used at temperatures up to about 125° C. for bleaching oils. At higher temperatures no bleaching advantage has ever been noted and consequently the clays were not used at higher temperatures. There is no relationship between selenium isomerization catalyst structures and the present clays, nor any theoretical basis for concluding that selenium or nitrogen oxides are either structurally or physically related in any manner to the acidic clays which are effective in the isomerization of jojoba oils.

Careful review of the clays effective for isomerization according to this invention shows that all have a montmorillonite crystallinity and have a pH of less than about 4.0 and preferably about pH 3.0. For convenience in later purification of the isomerized oil it is preferred that the acidic bleaching clay have less than about 0.25 wt% of residual acid. The pH and residual acidity are present as a result of the treatment of the clay with mineral acids to open the clay "books" and provide increased surface areas and exposure of internal crystalline bonding sites. While not wishing to be confined to any specific theory for the effectiveness of the specifically active clays, it is believed that the opening of the leaves of the crystalline clay "books" provides sites of suitable dimensions for the cis to trans reconfiguration.

As a result of the low pH of the clays and because of residual acidity of such clays, it has been found that the isomerates contain notable amounts of free acidity. As this is undesirable, it is preferable, after the desired degree of isomerization has been completed, to neutralize or remove this free acidity. This can be accomplished by contacting the isomerate, before or after removal of the suspended clay, with means for removal of such acidity. The isomerized oil may be contacted with solid basic substances such as NaOH, KOH, CaO, CaOH, $Na_2CO_3$, $NaHCO_3$. Concentrated solutions of these basic substances, may also be used provided that the basicity and ionization are adjusted to prevent saponification of the wax to the respective alcohol and salt of the acid. Other free acid removal means are solid ion-exchange resins or zeolites in the basic phase. The basic components thereof react with the free acidity and the so-neutralized oil is filtered from the reacted resin.

As pointed out above, the amount of clay used is not critical, but sufficient clay should be present to initiate and support the isomerization reaction. Excess clay has no effect on the reaction rate or degree of isomerization, but too much clay may absorb excess oil and thus interfere with the overall yield. Amounts of the preferred clay may range from at least about 0.5 wt% up to about 40 wt% based on the amount of oil being treated. Preferably the amount of clay should be in the range from about 1 to 10 wt% with the optimal range being about 2 wt%.

The contacting of the oil with the clay can take place in any convenient vessel which can provide and maintain the required temperature range. As there is a tendency for jojoba oil to oxidize either at the points of unsaturation or esterification, especially in contact with the expanded surface areas provided by the treated clays, it is preferred to maintain the reaction mass of oil and clay under an inert or protective atmosphere. Preferred as the inert atmosphere is nitrogen gas. The reaction vessel should be provided with suitable closures and piping to maintain such an inert atmosphere.

Upon completion of the isomerization in the reaction mass by suitable passage of time at the required temperature, the reaction mass is cooled to about 100° C. and the clay is separated from the transformed oil. Separation is preferably by filteration, but other separation means including centrifugation can be used.

The oil, after separation from the clay, can be treated for removal of the free acidity as mentioned above. In addition, any odorous components which may have developed can be steamstripped by passing steam through the isomerized oil.

It has been found that if the jojoba oil is refined before the isomerization step, that the development of undesirable color is minimized. The preferred refining procedure involves heating the jojoba oil to about 200° C. from one half to one and one half hours to coagulate and precipitate any proteinaceous material and denature any other impurities in the crude oil. These impurities may be filtered off. The oil is then decolorized by contacting with a decolorant. The decolorizing takes place at between 50° and 150° C. Suitable decolorants include neutral clays, acidic clays (including those which promote isomerization at temperatures above 150° C.), activated aluminas and activated carbons. Prior to isomerization the decolorizing step provides a product having very little color. When the decolorizing step is postponed until after completion of the isomerization, the decolorization by the above decolorants is virtually ineffective. The color materials which then develop after isomerization are not picked up by the decolorants and the resulting isomerized product is darker than the material from the preferred procedure. However, where color is not objectionable, as where the isomerized oil is used in highly pigmented materials or for dark leathers or where the isomerized material is to be further chemically reacted with sulphur compounds for the preparation of special lubricants, the darker isomerized materials, with or without decolorization, are adequate.

The isomerized materials prepared according to this invention are semi-soft solids having a room temperature consistency approximating butter. The melting points referred to supra and hereinafter are determined by methods appropriate for such materials. According to some testing standards, the terms "Hardening Point, "Softening Point", "Set Point" or "Congealing Point" are also used to describe this transition temperature. The method used for the Melting Point temperatures reported herein are according to EOA—Method H-1 "Determination of Congealing Point".

The preferred modes according to the present invention are described in the appended examples. Each mode is preferred for the specific product described. The products which result from each modification are for specific and different applications and thus the different modes are preferred for the different products.

EXAMPLE 1

Commercial jojoba oil (MP-5°-8° C.) 100 gms is heated to 100° C. and decolorized with 1 wt% of a substantially neutral (pH-6) bleaching clay (Tonsil L-80) for one hour. The oil is heated with agitation under nitrogen to 240° C. and admixed with 2 gms. of finely ground acid-treated montmorillonite clay (Tonsil Optimum Extra FF manufactured by Tonsil Mexicana SA). The clay has a pH of 3.5-3.0 and between 0.018 to 0.225% free residual acid. The reaction mass is stirred and maintained at the isomerization temperature of 240° C. Melting points are run on samples extracted from the mix every 0.5 hours. Curve A in the Figure shows that the isomerization is rapidly initiated and that the degree of isomerization reflected in the elevated melting points stabilizes in the range 30°-32° C. within 0.5 to 3.0 hours. The reaction mix is then cooled to 100° C. and the aciditic-clay is filtered from the mix. The isomerized oil having a melting point of 31.5° C., and Gardner color of about 7, is then contacted with powdered soda ash ($Na_2CO_3$) to neutralize any free acidity of the isomerate of jojoba oil.

EXAMPLE 2

The procedure of Example 1 is repeated, but at an isomerization temperature of 220° C. Curve B of the FIGURE shows the melting points obtained during the course of the reaction.

EXAMPLE 3

The procedure of Example 1 is repeated at an isomerization temperature of 200° C. Curve C shows the melting points obtained during the course of the reaction.

EXAMPLE 4

The jojoba oil is refined before decolorization by heating the commercial oil to 100°-200° C. to coagulate the protein and lipid impurities. The heated mass is then decolorized and the isomerization procedures of Examples 1-3 are repeated. The melting point curves obtained are similar to those of the FIGURE, but uniformly displaced to reflect a 2.5°-3.0° C. elevation in melting point of the isomerate of the refined jojoba oil.

EXAMPLE 5

Commercial jojoba oil, 500 lbs. is introduced into an agitated, stainless steel jacketed vessel under a nitrogen atmosphere and heated to 200° C. After one hour at 200° C., one percent (5 lbs.) of powdered decolorizing or bleaching clay (Tonsil L- 80-mfg by Tonsil Mexico SA) is introduced into the oil and mixed therewith for one hour. The clay and coagulum from the initial heating is then removed by filtration. The filtrate is then admixed with 2 wt% i.e. 10 lbs. of the acid-treated montmorillonite clay (pH $\leq 6$) (Tonsil Optimum or Tonsil Optimum Extra; or Tonsil Optimum FF; differing from each other only in residual acidity and particle size) and the resulting mass is heated to 240° C. for 3 hours until isomerization of the mass, as determined by the melting point of the successive abstracted samples, stabilizes. The reaction mass is cooled to 100° C. and the isomerizing clay is filtered off. The heated filtrate is conducted through a bed of powdered $Na_2CO_3$ of sufficient depth to remove any residual acidity from the isomerized oil. The neutralized oil, upon cooling to room temperature, had a light color (Gardner No. 5-6) and a semi-soft consistency of butter. The M.P. of the product is 34°-35° C. The product is suitable for direct topical application as a moisturizing and lubricating cream, as well as for formulation into various cosmetic formulations where such a high melting oil having the characteristic stability of jojoba oil is indicated.

The isomerized jojoba "butter" is also suitable for the treatment of leather to improve the suppleness. The isomerized oil reacts with sulphur compounds in a manner analogous to the cis-isomer oils to provide lubricants suitable for use at extreme temperatures and pressures. There are also other industrial uses.

We claim:

1. A process for the preparation of isomerates of jojoba oil having a melting point above about 25° C. which comprises the steps of contacting and reaching jojoba oil with an acidic-bentonite-type clay at temperatures in the range 150°-350° C. for a time sufficient to provide an isomerate having a melting point in the range 25° to at least about 44° C.

2. The process according to claim 1 wherein said clay is a comminuted montmorillonite, expanded and acid-treated montmorillonite having a pH less than about 4 and less than about 0.25 wt % residual acid.

3. The process according to claim 1 wherein the oil is contacted with from about 0.005 to about 40 wt% of said clay.

4. The process according to claim 1 wherein said contacting is conducted in an inert atmosphere.

5. The process according to claim 4 wherein said atmosphere is a nitrogen atmosphere.

6. The process according to claim 3 wherein the amount of said clay ranges from about 0.5 to about 5 wt% of said oil.

7. The process according to claim 6 wherein said amount is about 2 wt% of said oil.

8. The process according to claim 1 wherein an isomerate having a melting point of about 20°-29° C. is obtained by contacting the oil with about 2 wt% of an acid-treated montmorillonite clay having a pH of about 3-3.5 at a temperature of about 200° C. for about at least 1.0 hours.

9. The process according to claim 1 wherein an isomerate having a melting point in the range 27°-30° C. is obtained by contacting the oil with about 2 wt% of an acidic montmorillonite clay having a pH of 3-3.5 for about 1.0 hour at 220° C.

10. The process according to claim 1 having a melting point of about 30°-35° C. is obtained by contacting the oil with about 2 wt% of an acidic montmorillonite clay having a pH of about 3-3.5 for at least 0.5 hours at a temperature about 240° C.

11. The process according to claim 1 wherein the jojoba oil is refined by heating the oil to about 200° C. for about 1 hour to coagulate and precipitate proteins and other liquid impurities before isomerization.

12. The process according to claim 11 wherein said refining also includes contacting said oil with at least one decolorant selected from the group consisting of neutral pH bleaching-clay; activated-aluminas and activated-charcoal.

13. The process according to claim 11 wherein said refining includes decolorizing said oil after coagulation and precipitation -pH bleaching bentonite clay by contacting said oil with a neutral.

14. The process according to claim 1 wherein the reaction mass of oil and clay is cooled to about 50°-100° C., and filtered to remove said clay after completion of the isomerization.

15. The process according to claim 14 wherein the reaction mass is neutralized by contacting said mass with a basic substance in powder or solution form to reduce any free-acidity in the isomerate before filtration.

16. The process according to claim 14 wherein said isomerate is steam-stripped of odorous impurities after removal of said clay.

17. The isomerate of jojoba oil having a melting point in the range 25°-44° C. prepared by the process according to claim 1.

18. The product according to claim 17 is free from selenium, nickel, sulphur or nitrogen-oxide catalytic residues.

* * * * *